(12) United States Patent
Kampf et al.

(10) Patent No.: US 7,129,347 B2
(45) Date of Patent: Oct. 31, 2006

(54) METHOD FOR PURIFYING CAPROLACTAM FROM WASTE CONTAINING POLYAMIDE USING UV RADIATION

(75) Inventors: Rudolf Kampf, Haingründau (DE); Reinhard Wolf, Rodenbach (DE); Joachim Seelig, Biebergemünd (DE)

(73) Assignee: Zimmer Aktiengesellschaft, Frankfurt (DE)

(*) Notice: Subject to any disclaimer, the term of this patent is extended or adjusted under 35 U.S.C. 154(b) by 0 days.

(21) Appl. No.: 10/897,472

(22) Filed: Jul. 23, 2004

(65) Prior Publication Data

US 2005/0056532 A1     Mar. 17, 2005

(30) Foreign Application Priority Data

Jul. 23, 2003  (DE) ................ 103 33 539

(51) Int. Cl.
 *C07D 201/12*  (2006.01)
(52) U.S. Cl. .................................... 540/540
(58) Field of Classification Search ........... 540/540
 See application file for complete search history.

(56) References Cited

U.S. PATENT DOCUMENTS

| 2,752,336 | A | 6/1956 | Boon et al. |
| 2,813,858 | A | 11/1957 | Joris |
| 3,977,952 | A | 8/1976 | Knoevenagel et al. |
| 4,107,160 | A | 8/1978 | Dicoi et al. |
| 4,148,792 | A | 4/1979 | Danziger et al. |
| 4,605,672 | A | 8/1986 | Toth et al. |
| 5,359,062 | A | 10/1994 | Fuchs et al. |
| 5,598,980 | A | 2/1997 | Dilly-Louis et al. |
| 5,637,700 | A | 6/1997 | Fuchs et al. |
| 5,656,757 | A | 8/1997 | Jenczewski et al. |
| 5,990,306 | A | 11/1999 | Mayer et al. |
| 6,056,633 | A | 5/2000 | Sesena et al. |
| 6,095,441 | A | 8/2000 | Unkelbach et al. |
| 6,111,099 | A | 8/2000 | Frentzen et al. |
| 6,187,917 | B1 | 2/2001 | Mayer et al. |
| 6,579,979 | B1 | 6/2003 | Leconte |
| 2002/0030014 | A1 | 3/2002 | Leconte |

FOREIGN PATENT DOCUMENTS

| DE | 889199 | | 7/1953 |
| DE | 887 199 | | 8/1953 |
| DE | 910 056 | | 4/1954 |
| DE | 1105420 | * | 4/1961 |
| DE | 2408778 | | 9/1975 |
| DE | 24 16 573 | | 10/1975 |
| DE | 25 07 744 | | 9/1976 |
| DE | 19 719 734 | | 11/1998 |
| EP | 0 676 394 | | 10/1995 |
| EP | 0 681 896 | | 11/1995 |
| EP | 0 875 504 | | 11/1998 |
| EP | 0 875 505 | | 11/1998 |
| EP | 0 876 847 | | 11/1998 |
| IN | 142150 | | 6/1977 |
| JP | 5313636 | | 11/1993 |
| JP | 08099954 | | 4/1996 |
| JP | 2000038377 | | 2/2000 |

OTHER PUBLICATIONS

Brandup, et al., "Die Wiederverwertung von Kunstsoffen", (The Recycling of Plastics), Verlag Carl Hanser Munich, Vienna, 1995, pp. 513-520.
Organikum, Organisch-chemisches Grundpraktikum, Veb Deustscher Verlag der Wissenschaften, Berlin 1988, pp. 54-59. (English Translation).

* cited by examiner

*Primary Examiner*—Bruck Kifle
(74) *Attorney, Agent, or Firm*—Michael Best & Friedrich LLP

(57) ABSTRACT

The invention relates to a method for the continuous production of caprolactam from waste containing polyamide, comprising
 a) depolymerisation of the waste containing polyamide, whereby a caprolactam raw material and, where applicable, a flow containing secondary constituents or additives is obtained, and
 b) irradiation of the caprolactam raw material with UV radiation.

13 Claims, 1 Drawing Sheet

Figure 1:
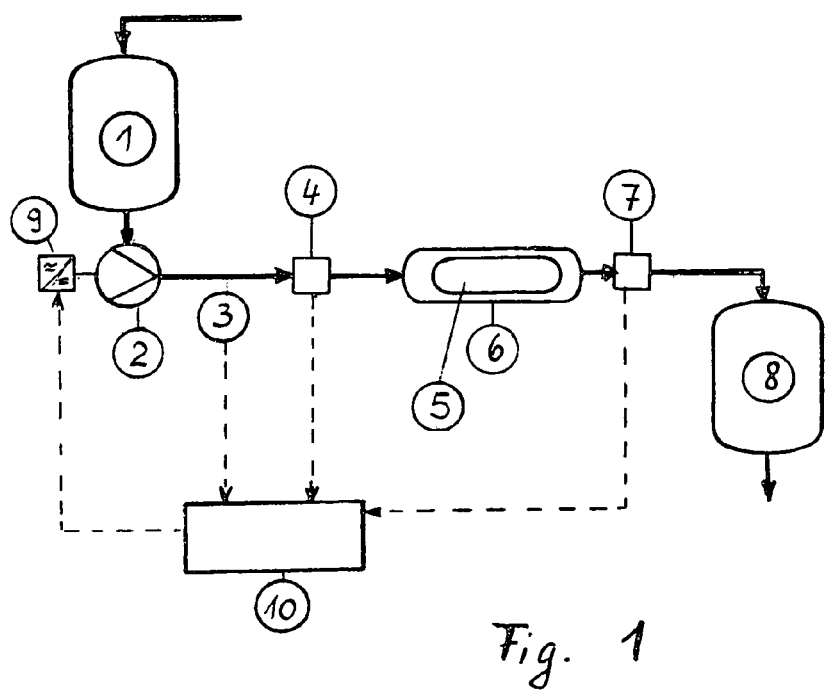

METHOD FOR PURIFYING CAPROLACTAM FROM WASTE CONTAINING POLYAMIDE USING UV RADIATION

RELATED APPLICATIONS

This application claims the foreign priority under 35 USC §119 of German Patent No. 10333539.0 filed on Jul. 23, 2003.

This invention relates to an optionally continuous and economical method for purifying caprolactam from polyamide waste, suitable for polycondensation to polyamide 6. In particular this invention relates to a method for the continuous production of caprolactam from waste containing polyamide with irradiation of the caprolactam raw material with UV radiation.

During the processing of recycled consumer articles, which have been used for many years, or products which originate from a collection of plastics, high quality caprolactam can only be produced with high levels of technology, energy and costs. For example, methods are known with the aid of which it is possible to obtain a pure caprolactam from polyamide waste through sorting, processing and purification stages. The steps they describe, in particular the addition of potassium permanganate, as also described in the U.S. Pat. Nos. 6,187,917, 2,752,336, 4,148,792 and 5,637,700, are regarded as essential for achieving a good colour value and a high quality caprolactam with good colour quality. Because plastic products are always adapted to the field of application, they contain manufacturer-specific and production-specific additives, dyes, stabilisers, glass fibres, etc. which impair the production of caprolactam with a good colour value. Therefore, with the economically efficient recycling of polyamide the breakdown into monomers is inevitable if a product is to be produced which is not different from goods produced out of monomers via the synthesis route.

It is also known that a caprolactam/water mixture, which is obtained after the depolymerisation, can be concentrated by fractional distillation, whereby it has in turn shown to be beneficial with regard to the purity of the caprolactam to continuously monitor secondary constituents by analyses and on-line measurements and to control the operating conditions such as, for example, temperature, pressure and return-feed ratio, such that the best possible removal of the undesired secondary products is achieved. Despite the further measures described, potassium permanganate must be added to improve the colour and the double bond content. Consequently, this method also requires the disadvantageous separation of the arising manganese dioxide in separation and filter stages in order to obtain colour purity and purity of the solids.

For all the reasons outlined above it will be appreciated that chemical additives are conventionally needed for the processing of raw caprolactam obtained from a recycling plant to a product with good colour values. In practice the addition of potassium permanganate has been found to be advantageous, which works as a mild oxidising agent and which breaks down colorizing double bonds, aldehydes or other products arising through decarboxylation with the generation of manganese dioxide. However, a disadvantage is the separation of the resulting manganese dioxide through agglomeration and filtration equipment and the disposal of the solids containing metal salts.

Furthermore, methods are known in which hydrogen peroxide, ozone or ozone/oxygen mixtures are employed. These have the advantage that no residues are left behind, but due to the high reactivity of hydrogen peroxide, ozone or ozone/oxygen mixtures, they are difficult to dose. However, an overdose leads to a degradation of the product quality of the caprolactam.

Therefore, the object of this invention is to provide a method in which the substances, which cause the reduced colour quality in raw caprolactam from polyamide recycling, are removed without having to consume chemicals and without eliminating their residues.

The solution according to the invention is a method for the preferably continuous production of caprolactam from waste containing polyamide, comprising
  a) depolymerisation of the waste containing polyamide, whereby a caprolactam raw material and, optionally, a flow containing secondary constituents or additives is obtained, and
  b) radiation of the caprolactam raw material with UV radiation.

The waste containing polyamide used in the method according to the invention is preferably selected from used or contaminated polyamide 6 waste or polyamide 6 waste taken from the recycling circulation. The waste containing polyamide is especially selected from the group consisting of moulded parts containing polyamide, such as parts for vehicles, injection moulded parts with glass fibres and other additives containing polyamide and fibres, carpets, carpet floor coverings and other objects from daily life containing polyamide, such as clothing. The material containing polyamide which is fed into the depolymerisation may also contain non-polymers and other types of additives.

Before the depolymerisation in stage a) of the method according to the invention the waste containing polyamide can first preferably be sorted, so that it primarily contains polyamide 6 and the other remaining substances are separated.

Caprolactam is the monomer which is used to produce polyamide 6 from which parts for vehicles, injection moulded parts with glass fibres and other additives, fibres for yarn for carpets, carpet floor coverings and other objects from daily life are then produced. A large part of these materials is disposed of after their normal use and only a small part is passed on for plastics recycling and recovery. The polyamide 6 products are usually not the only plastic materials consisting of amide groups and which are contained in a collection. Other polyamides arise which have been formed from various diacids and diamines. Therefore, preferably identification and sorting of the individual polyamide product groups is carried out before depolymerisation.

The processing of polyamide 6 waste after normal usage of the polyamide 6 can be carried out as described in various patents, for example DE 197 19 734, EP 0 681 896, U.S. Pat. No. 5,598,980, DE 241 65 73, DE 250 77 44, and comprises the identification and sorting of non-polyamide 6 goods, their pulverisation and separation of contaminated and foreign constituents. For the separation of the individual components, such as for example arise in the breaking down of carpets in the form of foam backing, pile and substrate, preferably multi-stage sink-and-float methods are used, in the course of which floatation of the lighter fraction, such as polypropylene web, and sinking of heavier, filled carpet backing occurs by means of centrifuging and salt solutions of different densities. A polyamide 6 fraction obtained according to this method is freed of clinging salts by washing and drying in a continuous process and passed to depolymerisation via an extruder.

In the depolymerisation, cracking of the polymer chains occurs for example according to methods known from DE 88 71 99, EP 0 875 504, DE 91 00 56, U.S. Pat. No. 4,605,762 and/or JP 53-13636 using phosphoric acid and introduced steam drives off the ensuing caprolactam as a water vapour mixture.

The depolymerisation in stage a) of the method according to the invention is preferably carried out at a temperature of about 180 to about 300° C. and at pressures of about 0.5 to about 2 bar. In addition, preferably a basic or acidic catalyst, such as phosphoric acid, is added. The reaction conditions during the depolymerisation are adapted preferably to the changing composition of the raw material charged during the process, namely of the waste containing polyamide. For example, the steam temperature can be increased, larger amounts of steam can be used, the molar ratio of phosphoric acid to polyamide can be varied and/or the pressure can be increased or reduced.

The caprolactam raw material irradiated with UV radiation in stage b) is the caprolactam raw material obtained after the depolymerisation in stage a). This is preferably a caprolactam solution, in particular an aqueous caprolactam solution with a content of caprolactam between 5% by mass and 99% by mass, preferably 25% by mass to 90% by mass.

The UV radiation in stage b) of the method according to the invention can be carried out with any known UV radiator. Preferably an immersible probe with a UV radiator is immersed in the caprolactam raw material, especially in a reactor, in which the immersible probe is arranged and the caprolactam raw material flows around it. Preferably the flow rate of the aqueous caprolactam solution is between about 10 mm/s and about 10 m/s, advantageously between about 10 cm/s and about 3 m/s. The radiated power is preferably in the range between about 0.01 watt/m$^2$ and about 10 kW/m$^2$, preferably 0.1 watt/m$^2$ to 1500 watt/m$^2$. Preferably broadband UV radiation sources are used which exhibit maximum emissions in the spectral range between 150 nm and 500 nm, preferably between 180 nm and 200 nm, in particular between 220 nm and 290 nm. For achieving a broadband spectrum a number of radiators of different maximum wavelengths, such as for example many high pressure radiators or medium pressure radiators at 180 nm and 220 nm as well as low pressure radiators at 260 nm can also be combined. Multi-emission UV radiators, such as for example in the product range from the company Heraeus, which have many emission maxima in the wavelength range between 200 and 600 nm, are preferred.

Stage b) of the method according to the invention is carried out at least once. It can however be carried out at least twice. The number of times stage b) of the method is carried out depends on the device used, in particular on the UV radiator used. A UV radiator can only be controlled to a limited extent with respect to its power. When processing caprolactam from recycling plants, various product quality levels and purity levels of the caprolactam must be expected. In order to take into account the changing requirements and not to radiate too highly, then with the method described a circulatory passage is selected in which the desired quality is produced by means of the number of circuit passes at constant radiator power. The desired quality is consequently assured in that automatic analytical devices acquire the spectrum of the aqueous caprolactam solution before entry into the UV radiator and after exit out of the UV radiator and passes under UV radiation are made until the quality criterion defined as the permanganate number is attained or undercut, as described in detail below.

The amount of radiation or the number of stages b) carried out depends on whether the caprolactam raw material already indicates the desired properties after one pass of stage b). If this is not the case, stage b) is carried out as many times as required in order to obtain the desired properties. In particular, the number of passes of stage b) or the amount of radiation depends on which intensity the analytical detector indicates after the passage of stage b), for example at the exit of a radiation chamber, as the output variable. If the change between a measured input variable before stage b) and the measured output variable after stage b) is too low and a specified quality criterion is not achieved, then a valve for the further transport of the caprolactam raw material is not released or opened, i.e. the material circulates as often as necessary until it achieves its quality specification. The specifying variable or quality criterion is especially the light transparency at 410 nm and 420 nm.

Preferably the irradiation is carried out by at least one UV radiator, especially 1 to 10 UV radiators.

The caprolactam raw material irradiated in stage b) of the method according to the invention, especially the caprolactam solution, may, during continuous reprocessing of polyamides, be subject to strong variations of the input products and the raw caprolactam composition. Therefore it is preferable, before carrying out stage b) of the method according to the invention to achieve a colour improvement, to pass the caprolactam raw material continuously through a light-transmitting cell and to continuously measure the light transmission, preferably in a spectral range from 200 nm to 1010 nm. The light transmission values measured in this way, in particular in a spectral range from 200 nm to 1010 nm, can be passed to a microcomputer for storage as the input variable.

Preferably, after carrying out stage b) of the method according to the invention, in particular at the end of a reactor with the UV radiator, another analytical station can be arranged, which measures the light transmission of the caprolactam material irradiated with the UV radiation, preferably in the spectral range from 200 nm to 1010 nm, and passes it to a microcomputer for storage as the output variable. Consequently, with continuously varying composition of an aqueous caprolactam flow the effects of the UV reactor on the product quality can be examined and saved via a calibration mode.

For the calibration of the measurement device caprolactam solutions with a very poor permanganate colour value, i.e. with a high absorption in the range of the wavelengths 410 nm and 420 nm, are determined using conventional analytical technology and set and measured by the dilution to intermediate values or lower light absorptions. The criteria and standard measurement methods are described below.

This caprolactam raw material resp. these caprolactam solutions are passed through measurement cells before and after stage b), and the light absorption is passed on to the control computer, where it is compared with the values occurring during operation. The criteria for classification as good quality can be adjusted by the plant operator and changed by manual entry.

The calibration phase can be followed by an evaluation phase. If it is found in the evaluation phase that the output variable, i.e. the light transmission of the caprolactam material obtained in stage b), deviates from the desired value, flow with the UV irradiation in stage b) can be increased or decreased. This can be preferably done in that a transport mechanism determining the flow through the UV reactor is provided with a measurement device for measuring the transported quantity and an inverter phase control for controlling the speed and quantity to be transported.

In particular through the measurement of the light transmission of the caprolactam raw material before stage b) and of the light transmission of the caprolactam material obtained after stage b), the variation found for constant radiator power can be regulated by adapting the flow or the dwell time in stage b), i.e. in the irradiation chamber. In particular the flow can be retarded and/or stage b) can be passed through several times if the output variable does not have the desired value, whereby the product quality is kept constant.

Since, as described above, during the continuous reprocessing of polyamides strong variations in the input product composition can occur and therefore also variations in the raw caprolactam composition can arise, it has proven extremely advantageous if the product, namely the caprolactam raw material, entering stage b) of the method according to the invention for achieving a colour improvement is passed continuously through a light-transparent cell and is tracked with regard to variations and quality according to the previously quoted criteria by continual tracking of the light transmission in a spectral range from 200 nm to 1010 nm. Furthermore, its has been proven to be very advantageous if the light transmission values in a spectral range from 200 nm to 1010 nm are passed to a microcomputer for storage as the input variable. In the next step following quality control, i.e. in stage b) of the method according to the invention, the caprolactam raw material, especially the caprolactam solution, is subjected to a UV radiator by which products such as aldehydes, ketones or unsaturated hydrocarbons are oxidised.

Preferably the caprolactam raw material to be irradiated in stage b) of the method according to the invention can be collected before passage to stage b) at least in one buffer vessel and, where applicable, after the analysis of the light transmission in a spectral range from 200 nm to 1010 nm and recording of the input variable, it can be subjected to UV irradiation at least once, in particular in a reactor with a UV radiator, whereby the caprolactam raw material is passed to the irradiation of stage b) by at least one transport mechanism.

The caprolactam obtained following the method according to the invention is of high purity and suitable for the polycondensation of high quality polyamide 6 and does not differ from a product originating from industrial production with regard to the colour value which is determined by photometric methods. In quality control the following methods have become established for assessing caprolactam:

In the first case a 1% aqueous caprolactam solution is defined after the addition of 1% by mass of a 0.01 n $KMnO_4$ solution at 25° C. after 250 seconds at the wavelength of 410 nm according to the Klett-Summerson method as the 100-times value of the extinction as the quality criterion or as the permanganate absorption number after 600 seconds at a wavelength of 420 nm. According to Klett-Summerson the 100-times value of the extinction should not exceed 7 and with the permanganate absorption number the 100-times value of the extinction should not exceed 5.

The second method prefers the visual assessment with a standard solution. 1 ml of a 0.01 n potassium permanganate solution is added to 100 ml of an aqueous solution containing 1 to 3% by mass of caprolactam at a temperature of 20° C. and the time recorded until colour equality is obtained compared to a standard solution. As a standard, aqueous solutions of cobalt nitrate/cobalt chloride as aqueous solutions mixed with potassium bichromate/copper sulphate are usual. A caprolactam is regarded as qualitatively good if a one-percent solution, mixed with potassium permanganate attains the same colour in 10000 to 40000 seconds when measured against a solution of 1 l of water containing 2.5 g of $Co(NO_3)_2 \cdot 6H_2O$ and 0.01 g $K_2CrO_7$.

In contrast to a caprolactam production from pure raw materials, in which there is no disturbance of the continuous operation due to the varying composition of the incoming product flow, the product quality variations resulting from the changing composition of the input material can be regulated and compensated using the method according to the invention.

The method according to the invention advantageously avoids the additional, cost- and energy-consuming process steps of trapping and separating solids in that the caprolactam raw material, in particular a caprolactam solution, is improved with regard to colour properties by irradiation with UV radiation.

The method according to the invention with the application of UV irradiation, for example using immersible probes, is advantageous compared to the state of the art in that no chemicals need to be employed. With the addition of peroxide chemicals or also with permanganate, then due to inexact acquisition of the required amount and where a case of overdosing occurs, disturbances arise in the following process stages as a result of their unreacted proportions. Overdosing also gives rise to costs which reduce the economic efficiency of a method. If too little is used, the quality cannot be achieved.

Figure 2:
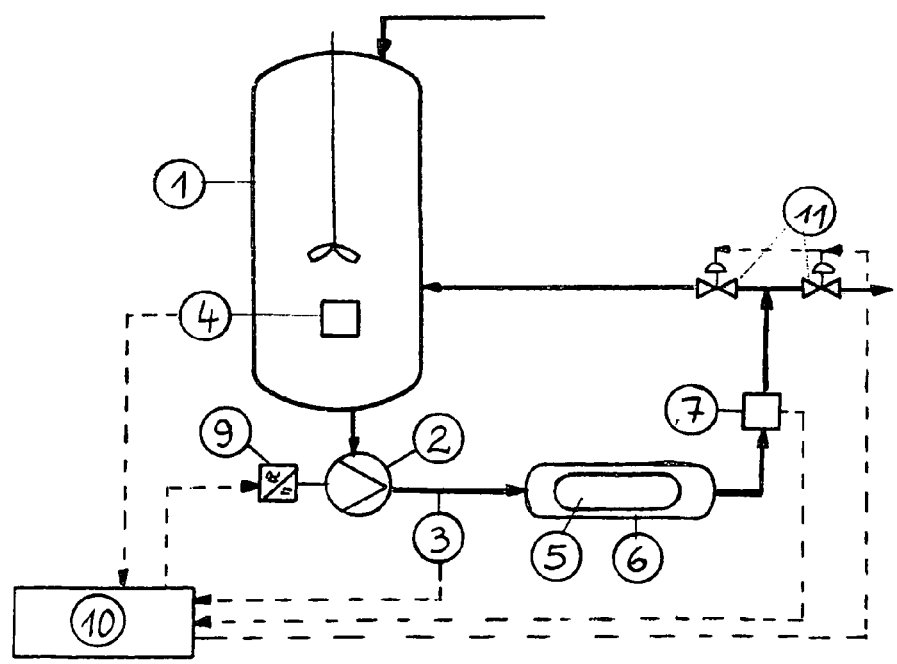

FIGS. 1 and 2 show suitable equipment for carrying out stage b) of the method according to the invention with 1 Buffer or collecting vessel
2 Transport mechanism
3 Flow measurement instrument
4 Analytical device, input inspection, spectrometer Zeiss MCS 320+MCS 340
5 UV radiator, e.g. Heraeus NIQ 120/80
6 Tubular reactor
7 Analytical device, output inspection, spectrometer Zeiss MCS 320+MCS 340
8 Buffer or collecting vessel, output for further processing
9 Inverter phase control for transport mechanism flow control
10 Microcomputer-based acquisition, evaluation and control system, control of the throughput dependent on 4, 7
11 Distributor valves, return to collection vessel and output for further processing The method according to the invention can be carried out in the systems shown in FIG. 1 or 2. To achieve this, the caprolactam raw material obtained after stage a) is collected in a buffer 1, in which an analytical device 4 for measuring the input magnitude of the light transmission of the caprolactam is arranged and is then passed to the UV radiator 5 using a transport mechanism 2 after which a flow measurement device 3 is arranged, the said radiator being located in a tubular reactor 6. The UV radiators 5 used according to the invention have a permanently defined radiation power in watt/m$^2$ which depends on the required throughput rate. A UV radiator can, once ignited, only be controlled in a narrow range. If the mass to be radiated changes, which is related to a certain radiation power in the design, then disadvantageously either underdosing or overdosing occurs. To prevent this, advantageously the product to be radiated, namely the caprolactam raw material, is collected in the buffer vessel 1 and passed in a regulated manner after analysis by the analytical device 4 in a spectral range from 100 nm to 1010 nm to the tubular reactor 6 with the UV radiator 5 by the transport mechanism 2.

An inverter phase control 9 is arranged on the transport mechanism 2 for controlling the throughput rate through the tubular reactor 6.

After the tubular reactor 6, the caprolactam obtained after irradiation is passed through an analysis device 7 in which the light transmission of the obtained caprolactam is measured as the output variable and recorded. Then, the obtained caprolactam is stored in a further buffer 8 until it is used further and until being polymerised to polyamide 6, as shown in FIG. 1. As illustrated in FIG. 2, the caprolactam obtained after stage b) can also be passed to a distributor valve 11 and depending on the measured output variable be directly processed further or passed back to the buffer 1 for further irradiation.

Furthermore, the system comprises a microcomputer 10 in which the input and output variables measured in the analytical devices 4 and 7 are stored. The microcomputer 10 is also connected to the flow measurement device 3 and to the inverter phase control 9 and controls, in a closed-loop manner by means of the inverter phase control 9, the flow rate through the tubular reactor 6 depending on the measured input and output variables and the flow rate.

The analysis station 7, which measures the light transmission in the spectral range from 200 nm to 1010 nm and passes it to the microcomputer 10 for storage as the output variable, is used to examine the effects of the UV reactor on the product quality by means of a so-called calibration mode with a continuously changing composition of an aqueous caprolactam flow and to save the said effects. The evaluation phase, which follows the calibration phase, is carried out under the aspects of obtaining the best product quality at the reactor output by changing the throughput at constant irradiation power and a changing composition of an aqueous caprolactam flow. For this purpose, the pump 2, which determines the flow through the UV reactor 6, is provided with a measurement of the flow 3 according to the state of the art and a phase-controlled inverter 9 for the closed-loop control of the speed and transported quantity. Using these measures, it is possible advantageously to control the variations found in the entry analysis station 4 at constant radiator power 5 by adapting the throughput or the dwell time in the irradiation chamber and to keep the product quality constant.

The invention is explained in the following based on examples.

EXAMPLE 1

In the operation of a production plant for the processing of polyamide 6 waste, such as for example those described in the various patents DE 19719734, EP 0681896, U.S. Pat. No. 5,598,980, DE 2416573 and DE 2507744 the identification and sorting of non-polyamide 6 articles occurs, with their pulverisation and separation from contamination and other additives. For the separation of individual components, as arise for example during the breaking down of carpets in the form of foam backing, pile and substrate, multi-stage sink-and-float methods are preferably used, in the course of which the flotation of the lighter fraction, such as polypropylene webbing and the sinking of the heavier filled carpet backing takes place using centrifuging and salt solutions of various densities. A polyamide 6 fraction obtained according to this method is freed from clinging salts by washing and drying in a continuous method and passed to the depolymerisation via an extruder. In the depolymerisation, cracking of the polymer chains occurs using phosphoric acid, for example according to the methods known from DE 887199, EP 0875504, DE 910056, U.S. Pat. No. 4,605,762 and JP 53-13636, and introduced steam drives off the arising caprolactam as a water vapour mixture.

A disadvantage with the known methods is that this does not supply any highly pure caprolactam which can be used for the production of polyamide 6. With the previous practice during the purification of caprolactam obtained from carpets of polyamide 6 or aqueous caprolactam solution, the procedure is used of adding potassium permanganate. A disadvantage here is that the permanganate added to the caprolactam is reduced, producing an ensuing separation of manganese dioxide.

If the caprolactam or its aqueous solution is passed to a device according to the embodiment in FIG. 1 of the invention, then by using the claimed method with the quality features listed in Table 1, both product-specific as well as economic advantages arise compared to other methods. The results can be taken from Table 1.

EXAMPLE 1

Raw caprolactam solution is fed into a vessel 1 and the spectral properties acquired by the analytical unit 4 in front of the irradiation apparatus. At the bottom of the vessel 1 solution is drawn off by a pump 2, 9, which is closed-loop controlled for rotation and throughput. The solution flows through the flow measurement point 3, it is subjected to the broadband UV radiator 5 with the defined power in the reactor 6 and its modification is checked in the analytical unit 7. The control valves 11 receive the commands from the microcomputer evaluation and control unit 10 for discharging certain amounts for further processing and return to the storage vessel 1.

TABLE 1

| Method | Oxidation agent | Permanganate number sec | Permanganate number Degree of variation sec | UV transmission % | UV transmission Degree of variation % | Cost comparison Investment Consumption Energy |
|---|---|---|---|---|---|---|
| Industrial | Unknown | >10,000 | | >85 | | — |
| Comparison method | Permanganate | Min. 5000 Max. 8000 | 3000 | Min. 72 Max. 87 | 15 | 100 |
| Comparison method | Hydrogen peroxide | Min. 5500 Max. 8000 | 2500 | Min. 80 Max. 85 | 12 | 98 |
| Example 1 | UV radiator | Min. 10,000 Max. 11,000 | 1000 | Min. 88 Max. 92 | 5 | 90 |

EXAMPLE 2

Raw caprolactam solution is fed into a vessel 1 and the spectral properties acquired by the analytical unit 4 in the reactor. At the bottom of the vessel 1 solution is drawn off by a pump 2, 9, which is closed-loop controlled for rotation and throughput. The solution flows through the flow measurement point 3, it is subjected to the broadband UV radiator 5 with the defined power in the reactor 6 and its modification is checked in the analytical unit 7. The control valves 11 receive the commands from the microcomputer evaluation and control unit 10 for discharging certain amounts for further processing and return to the storage vessel 1.

The invention claimed is:

1. Method for the production of caprolactam from waste containing polyamide, comprising
   a) depolymerisation of the waste containing polyamide, whereby a caprolactam raw material, optionally, a flow containing secondary constituents or additives is obtained, and
   b) irradiation of the caprolactam raw material with UV radiation.

2. Method according to claim 1, whereby the waste containing polyamide is selected from the group consisting of used, contaminated polyamide 6 waste or polyamide 6 waste obtained from the recycling circulation, moulded parts containing polyamide, injection moulded parts with glass fibres containing polyamide and other additives and fibres, carpets, carpet floor coverings containing polyamide and other objects containing polyamide from daily life.

3. Method according to claim 1, whereby before stage b) the light transmission of the caprolactam raw material is measured and recorded as the input variable.

4. Method according to claim 3 whereby for the measurement of the light transmission the caprolactam raw material is continuously passed through a light-transparent cell and is measured in a spectral range from 200 nm to 1010 nm by continual tracking of the light transmission.

5. Method according to claim 3, whereby the input variable of the light transmission in a spectral range from 200 nm to 1010 nm is passed to a microcomputer for storage.

6. Method according to claim 1, whereby the caprolactam raw material to be irradiated is collected in at least one buffer vessel before passing through the stage b) and after acquisition of the light transmission in a spectral range from 200 nm to 1010 nm is fed for carrying out stage b) to a reactor with UV radiator by at least one transport mechanism for irradiation.

7. Method according to claim 1, whereby the irradiation in stage b) occurs by at least one UV radiator.

8. Method according to claim 7, whereby stage b) is carried out in the at least one reactor with at least one UV radiator enclosed by flow.

9. Method according to claim 1, whereby after stage b) the light transmission of the caprolactam obtained after stage b) is measured and recorded.

10. Method according to claim 9, whereby the measurement of the light transmission is carried out in the spectral range from 200 nm to 1010 nm and is passed to a microcomputer for saving as the output variable.

11. Method according to claim 1, whereby the effects of the UV reactor on the product quality are examined by means of a calibration mode with continually varying composition of an aqueous caprolactam solution and are stored.

12. Method according to claim 11, whereby an evaluation phase follows the calibration phase.

13. Method according to claim 4, whereby the input variable of the light transmission in a spectral range from 200 nm to 1010 nm is passed to a microcomputer for storage.

* * * * *